US008826722B2

(12) United States Patent
Odendall

(10) Patent No.: US 8,826,722 B2
(45) Date of Patent: Sep. 9, 2014

(54) METHOD FOR DETERMINING A DELAY TIME OF A PRE-CATALYTIC CONVERTER LAMBDA PROBE AND METHOD FOR DETERMINING THE OXYGEN STORAGE CAPACITY OF AN OXYGEN STORE

(75) Inventor: Bodo Odendall, Lenting (DE)

(73) Assignee: Audi AG, Ingolstadt (DE)

(*) Notice: Subject to any disclaimer, the term of this patent is extended or adjusted under 35 U.S.C. 154(b) by 345 days.

(21) Appl. No.: 13/210,643

(22) Filed: Aug. 16, 2011

(65) Prior Publication Data

US 2012/0055231 A1 Mar. 8, 2012

(30) Foreign Application Priority Data

Sep. 8, 2010 (DE) ........................ 10 2010 044 661

(51) Int. Cl.

| | |
|---|---|
| ***G01N 33/497*** | (2006.01) |
| ***F02D 41/14*** | (2006.01) |
| ***F02D 41/02*** | (2006.01) |
| *F01N 3/08* | (2006.01) |
| *F01N 11/00* | (2006.01) |

(52) U.S. Cl.

CPC ........ *F02D 41/1441* (2013.01); *F02D 2250/14* (2013.01); *F01N 3/0864* (2013.01); *F01N 11/007* (2013.01); *F02D 2200/0816* (2013.01); *F01N 2550/02* (2013.01); *F02D 41/0295* (2013.01)

USPC ........................................................ 73/23.32

(58) Field of Classification Search

CPC ............ F02D 41/1441; F02D 41/0295; F02D 2250/14; F02D 2200/0816; F01N 3/0864; F01N 11/007; F01N 2550/02

USPC ........................................... 73/23.32, 114.72

See application file for complete search history.

(56) References Cited

U.S. PATENT DOCUMENTS

| | | | | |
|---|---|---|---|---|
| 4,502,444 | A * | 3/1985 | Rubbo et al. | 123/695 |
| 5,052,361 | A * | 10/1991 | Ono et al. | 123/688 |
| 6,371,096 | B1 | 4/2002 | Ohsaki et al. | |
| 6,901,741 | B2 * | 6/2005 | Kobayashi et al. | 60/274 |
| 7,269,996 | B2 | 9/2007 | Schnaibel et al. | |
| 7,387,011 | B2 * | 6/2008 | Fujiki et al. | 73/23.32 |
| 2006/0190159 | A1 | 8/2006 | Iihoshi et al. | |
| 2009/0313971 | A1 * | 12/2009 | Mueller-Stach et al. | 60/276 |
| 2010/0083743 | A1 | 4/2010 | Wehmeier et al. | |

FOREIGN PATENT DOCUMENTS

| | | |
|---|---|---|
| DE | 10 2005 032 456 A1 | 1/2007 |
| DE | 10 2008 042 549 A1 | 4/2010 |

* cited by examiner

*Primary Examiner* — Daniel S Larkin
(74) *Attorney, Agent, or Firm* — Henry M Feiereisen LLC

(57) ABSTRACT

The output signal of a pre-catalytic converter lambda probe and the output signal of a controller are used to determine an inherent delay time of the pre-catalytic converter lambda probe, for example due to aging of the probe, by measuring, for example, the separation between maxima in these output signals. The pre-catalytic converter lambda probe is installed in an exhaust gas system of an arrangement wherein an internal combustion engine operated under controlled conditions. The determined delay time can be used to determine the oxygen storage capacity of an oxygen store associated with a catalytic converter in the arrangement by determining with the pre-catalytic converter lambda probe the start of a time interval over which integration takes place, and determining the actual end time of the integration by adding the delay time to an end time determined from an output signal of the post-catalytic converter lambda probe.

4 Claims, 2 Drawing Sheets

METHOD FOR DETERMINING A DELAY TIME OF A PRE-CATALYTIC CONVERTER LAMBDA PROBE AND METHOD FOR DETERMINING THE OXYGEN STORAGE CAPACITY OF AN OXYGEN STORE

CROSS-REFERENCES TO RELATED APPLICATIONS

This application claims the priority of German Patent Application, Serial No. 10 2010 044 661.0, filed Sep. 8, 2010, pursuant to 35 U.S.C. 119(a)-(d), the content of which is incorporated herein by reference in its entirety as if fully set forth herein.

BACKGROUND OF THE INVENTION

The present invention relates to a method for determining a predetermined delay time of a pre-catalytic converter lambda probe in a predetermined arrangement. The invention also relates to a method for determining the oxygen storage capacity of an oxygen store associated with a catalytic converter is part of such predetermined arrangement.

The following discussion of related art is provided to assist the reader in understanding the advantages of the invention, and is not to be construed as an admission that this related art is prior art to this invention.

The predetermined arrangement is directed to an arrangement with an internal combustion engine, wherein the difference between an output signal of the pre-catalytic converter lambda probe and a desired signal is supplied as an input signal to a controller. The controller is typically implemented as a PI controller or PID controller. The output signal of the controller determines the air-fuel ratio of exhaust gas to which the pre-catalytic converter lambda probe is exposed through operation of the internal combustion engine. The output signal determines the quantity of injected fuel and supplied air of the internal combustion engine, which directly determines the air-fuel ratio in the exhaust gas. The delay time to be determined is the time by which an actual air-fuel ratio observed in the output signal of the pre-catalytic converter lambda probe is delayed.

In a predetermined arrangement of the aforedescribed type, the exhaust gas system, which typically includes in the outflow direction of the exhaust gas following the pre-catalytic converter lambda probe a catalytic converter with oxygen storage capability, is typically exposed to exhaust gas by changing the air-fuel ratio $\lambda$ changes between values greater than one and values less than one, i.e., alternatingly operating rich and lean. This is determined by the desired signal, which forms the basis for forming the difference with the response signal from the pre-catalytic converter lambda probe. Exposure with changing lambda is necessary to systematically compensate for possible errors. The oxygen storage capacity of an oxygen store associated with the catalytic converter is typically determined by filling the oxygen store in a defined manner through exposure to lean exhaust gas following a phase of exposure to rich exhaust gas, where the oxygen store was completely emptied, wherein the quantity of oxygen introduced per unit time is integrated over a time interval. The start of the time interval is typically triggered by the output signal of the pre-catalytic converter lambda probe when this output signal satisfies a predetermined criterion, e.g., crosses a threshold value.

When determining the oxygen storage capacity, the delay in the reaction of the pre-catalytic converter lambda probe to an air-fuel ratio has a direct effect on the measurement values. It is also a general interest to know this delay time.

It would be feasible to set the output signal of the pre-catalytic converter lambda probe in reference to the full signal. However, this simple comparison between "actual" and "desired" provides the correct result only for short delay times. Because the predetermined arrangement includes the controller, the delay in the reaction of the pre-catalytic converter lambda probe causes an immediate overshoot in the output signal of the controller. When the delay reaches a certain magnitude, a type of oscillation is produced where a temporal characteristic is no longer correlated with the aforementioned delay time itself.

It would therefore be desirable and advantageous to obviate prior art shortcomings and to provide an improved method for reliably determining the delay time in an arrangement of the aforedescribed type. It would also be desirable and advantageous to determine the oxygen storage capacity of the oxygen store by taking into consideration the determined delay time.

SUMMARY OF THE INVENTION

According to one aspect of the present invention, a method for determining a delay time of a pre-catalytic converter lambda probe during operation of an arrangement with an internal combustion engine includes the steps of supplying a difference between an output signal of the pre-catalytic converter lambda probe and a desired signal to a controller as an input signal, measuring an output signal of the controller, wherein the output signal determines an air-fuel ratio of the exhaust gas to which the pre-catalytic converter lambda probe is exposed during the operation, determining a first time when a first output signal of the controller satisfies a first predetermined criterion, and determining a second time following the first time when a second output signal of the pre-catalytic converter lambda probe satisfies a second predetermined criterion. The method further includes the steps of determining a time difference between the second time and the first time, said the time difference defining the delay time, and determining an actual air-fuel ratio of the exhaust gas to which the pre-catalytic converter lambda probe is exposed by determining the output signal of the controller at a time computed by adding the delay time to the second time.

The method according to the invention thus compares an actual output of the controller with an actual output of the lambda probe. The method is based on the recognition that the delay time is also included in the ratio of the two signals, allowing reliable determination. In particular, the inventor has recognized that the desired signal need not be considered at all when determining the delay time, but that the delay time can be obtained instead from an output signal of the controller.

By determining with the method a first time and a second time according to a respective predetermined criterion, these predetermined criteria can be suitably adapted to the properties of the predetermined arrangement during operation. The predetermined criteria directly define how the delay time is determined.

According to an advantageous feature of the present invention, the predetermined criterion may be identically defined for both output signals. By correlating the predetermined criterion with the curve shape of the respective output signals (of the controller and of the pre-catalytic converter lambda probe), the curve shape of the output signal of the controller and of the output signal of the pre-catalytic converter lambda probe are advantageously found to be identical or at least similar.

According to an advantageous feature of the present invention, the predetermined criterion implies that a maximum in the respective output signal is reached at the corresponding time to be determined, which prevents prevent an offset in the output signal of the pre-catalytic converter lambda probe from causing a faulty determination of the delay time.

According to another aspect of the invention, a method for determining oxygen storage capacity of an oxygen store associated with a catalytic converter of an arrangement with an internal combustion engine, wherein a pre-catalytic converter lambda probe is arranged upstream of the catalytic converter and a post-catalytic converter lambda probe is arranged downstream of at least one section of the catalytic converter, includes the steps of supplying a difference between an output signal of the pre-catalytic converter lambda probe and a desired signal to a controller as an input signal, measuring an output signal of the controller, said output signal determining an air-fuel ratio of the exhaust gas to which the pre-catalytic converter lambda probe is exposed during the operation, determining a first time when a first output signal of the controller satisfies a first predetermined criterion, determining a second time following the first time when a second output signal of the pre-catalytic converter lambda probe satisfies a second predetermined criterion, and determining a time difference between the second time and the first time, with this the time difference defining the delay time. The method further includes the steps of either removing as much oxygen as possible from the oxygen store and thereafter completely filling the oxygen store with oxygen to a certain level, or filling the oxygen store with as much oxygen as possible and thereafter completely removing oxygen from the oxygen store to a certain level, and determining a quantity of introduced or removed oxygen per unit time over a time interval, which starts at a third time when the output signal of the pre-catalytic converter lambda probe satisfies a third predetermined criterion, and is terminated at an end time which is computed by adding the delay time to a fourth time when an output signal of the post-catalytic converter lambda probe satisfies a fourth predetermined criterion.

In the method according to the invention for determining the oxygen storage capacity, a delay which occurs at the beginning of the measurement is therefore compensated by a corresponding delay at the end of the measurement. This is based on the recognition that this delay also affects the signals, meaning that the "correct" basic curve shape is shifted by exactly this delay.

According to an advantageous feature of the present invention, the third and/or the fourth predetermined criteria are satisfied when the output signal of the pre-catalytic converter lambda probe and/or of the post-catalytic converter lambda probe crosses a (corresponding, i.e., third or fourth) predetermined threshold value. This is typical for the way by which the boundaries of the time interval are determined.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Figure 1:
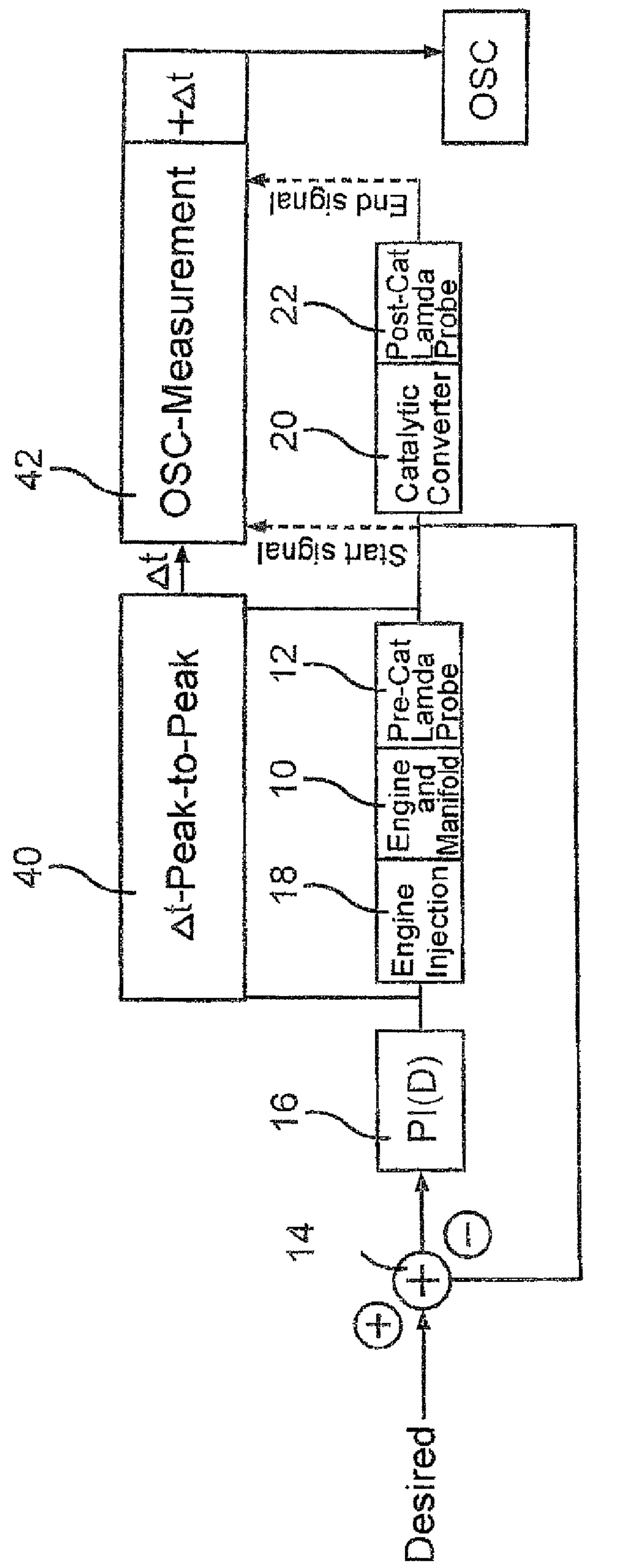
FIG. 1 a diagram describing the arrangement used to carry out the invention, and for describing the invention itself.

Throughout all the figures, same or corresponding elements may generally be indicated by same reference numerals. These depicted embodiments are to be understood as illustrative of the invention and not as limiting in any way. It should also be understood that the figures are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

Turning now to the drawing, and in particular to FIG. 1, there is shown a diagram describing the arrangement used to carry out the method according to the invention.

A desired curve shape of the air-fuel ratio to be adjusted in the exhaust gas of the internal combustion engine is defined for an internal combustion engine 10. The desired signal is defined in a physical unit (typically in Volt) used to measure the output signal of a pre-catalytic converter lambda probe 12. The inverted output signal of the pre-catalytic converter lambda probe 12 is added to the (non-inverted) desired signal in an adder 14, and the result of this addition is supplied to a PI controller or a PID controller 16. The output signal of the controller 16 directly determines the engine injection 18, and hence the operation of the engine 10. After combustion and the exhaust gas manifold, the exhaust gas then again reaches the pre-catalytic converter lambda probe 12. A catalytic converter 20 is arranged downstream of the pre-catalytic converter lambda probe 12 in the outflow direction of the exhaust gas, wherein the catalytic converter 20 includes an integrated oxygen store, and a post-catalytic converter lambda probe 22 is arranged downstream of at least one section of this oxygen store.

The pre-catalytic converter lambda probe 12 can have a delayed reaction, in particular due to aging effects of the probe 12. This will now be described with reference to FIG. 2:

The curve 24 shows the desired signal supplied to the non-inverted input of the adder 14. At the time 2.0 s, a jump occurs from a rich air-fuel ratio to a lean air-fuel ratio. If the pre-catalytic converter lambda probe reacts with a delay, then the output signal of the controller 16 has the characteristic shape of curve 26, i.e., it increases significantly above the maximum value in the curve 24. The output signal of the pre-catalytic converter lambda probe 12 then shows the curve shape 28. As can be seen, the actual air-fuel ratio overshoots significantly farther towards lean than intended by the predetermined desired value: for example, at the time 2.75 s to a value $\lambda$ greater than 1.2, whereas the desired value is 1.05. The same effect is manifested in an undershoot: at the time 3.6 s, the actual air-fuel ratio reaches a value of 0.78, whereas the desired value is 0.95.

The curve 30 shows the integral component in the output signal of the control of according to curve 26, and the curve 26 shows the proportional component. The oscillation in the signals is clearly visible.

It was recognized that the delay time Δt, by which a reaction of the pre-catalytic converter lambda probe 12 is delayed relative to an actual air-fuel ratio before the actual air-fuel ratio is observed in the output signal of the pre-catalytic converter lambda probe 12, can be determined based on the curves 26, on one hand, and the curves 28, on the other hand: basically, the time is determined when the curve 26 reaches a (local) maximum. This occurs, for example, at the time 2.3 s. Likewise, the time is determined when the curve 28 reaches a (local) maximum. This occurs, for example, at the time 2.7 s. The temporal spacing between these two times, when the respective maxima (peaks) are reached, is determined, i.e., Δt is measured from peak-to-peak. In the present example, Δt is exactly equal to 0.4 s.

This information is subsequently used for measuring the oxygen intake storage capacity (OSC measurement). The oxygen intake storage capacity is usually computed from the following formula $$OSC = 0.23\int_{t_a}^{t_b}(\lambda(t)-1)\dot{m}dt$$

For measuring the oxygen intake storage capacity, the oxygen store is first emptied, and then filled again, starting at a time $t_a$. The change in the desired behavior is typically determined from the signal of the pre-catalytic converter lambda probe which crosses a threshold value. When the oxygen store is completely filled, the signal from the post-catalytic converter lambda probe also crosses a (typically the same) threshold value, with the time of this later crossing being the boundary of the integral. The quantity 0.23·(λ(t)−1) is the quantity of oxygen introduced per unit time (at constant exhaust gas mass flow ṁ). The integrand is then the distance between the respective curve 24, 26, 28 and the line λ=1=cst.

Figure 3:
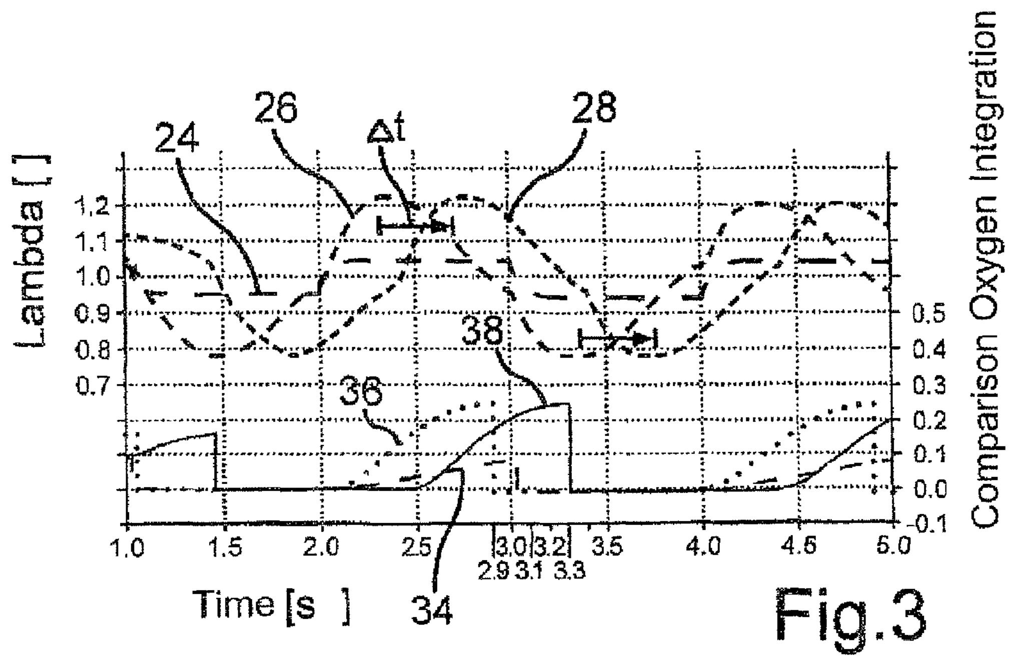
FIG. 3 the result of an integration for determining the oxygen storage capacity for several of the signals of FIG. 2, illustrating the method of the invention for determining the oxygen storage capacity of the oxygen store.

FIG. 3 shows the curve 34 which indicates how this integral would appear if the desired curve shape of curve 24 would be used as basis for the computation. The curve 36 shows how this integral would appear if the desired curve shape of curve 26 would be used, and curve 38 shows the same for the curve shape according to curve 28.

Is evident that the two curves 36 and 38 are shifted only by the delay time Δt.

The above formula (1) is based on the assumption that the values for $t_a$, $t_b$ and ·λ(t) have each be measured correctly. In actuality, however, a value $t_{a,\ mess}$ is determined for $t_a$, which is delayed by the time delay Δt, since $t_a$ is here measured based on the output signal of the pre-catalytic converter lambda probe 12 which has this intrinsic delay. On the other hand, the value for ·(t) is also obtained with the delay Δt, so that the correct λ(t) is obtained from $\lambda(t)=\lambda_{mess}\cdot(t+\Delta t)$. The following equation is then obtained:

$$OSC = 0.23\int_{t_{a,mess}-\Delta t}^{t_{b,mess}}(\lambda_{mess}(t+\Delta t)-1)\dot{m}dt.$$

With the transformation t'=t+Δt, the following equation is obtained:

$$OSC = 0.23\int_{t_{a,mess}}^{t_{b,mess}+\Delta t}(\lambda_{mess}(t')-1)\dot{m}dt'$$

In other words, a correct result for the oxygen storage capacity OSC is obtained, if the measurement integral starts at the actual time $t_{a,\ mess}$ measured with the pre-catalytic converter lambda probe and simultaneously the measurement values of the pre-catalytic converter lambda probe are used for the integration, as long as the integral is additionally terminated at a time that is delayed by Δt with respect to $t_{b,\ mess}$.

This can also be seen in FIG. 3:

The curve 38 has the same shape as the curve 36, so that an integration over the output from the controller would be correct. However, the start of the integration can be more easily determined for the curve 38. In the present example, this is the time shortly before 2.5 s. The integration should then not be terminated at the time 2.9 s, but must be continued with the time offset Δt until the time 3.3 s.

Figure 2:
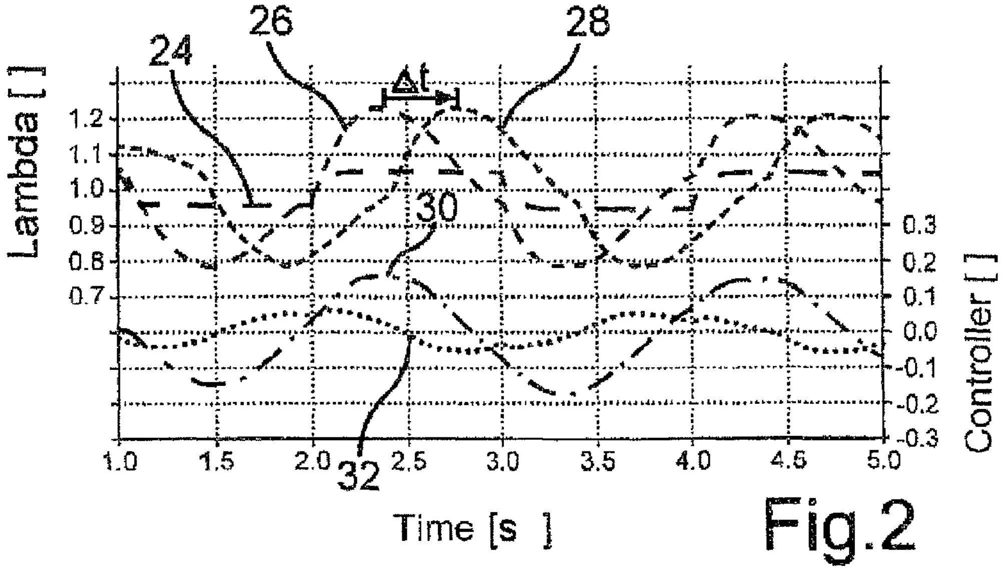
FIG. 2 several signals that can be obtained from the arrangement according to FIG. 1, based on which the time delay to be determined is defined.

The determination of the delay time in the reaction of the pre-catalytic converter lambda probe 12 to an actual air-fuel ratio described with reference to FIG. 2 can advantageously be used to correctly determine the oxygen storage capacity of the oxygen store associated with the catalytic converter 20. FIG. 1 shows that a unit 40 which determines the peak-to-peak time delay Δt in the curves 26 and 28 transmits the result of this determination onward to a unit 42 which performs the integration according to curve 38, wherein the output signal of the pre-catalytic converter lambda probe represents a start signal for the integration, the output signal of the post-catalytic converter lambda probe provides the end signal, and wherein the end signal is then delayed by the time Δt in order to arrive at the correct value for the oxygen intake storage capacity OSC.

The same approach as described above for the oxygen intake storage capacity applies likewise to the oxygen removal storage capacity, which is measured by initially completely filling the oxygen store with oxygen and subsequently removing oxygen in a defined manner.

While the invention has been illustrated and described in connection with currently preferred embodiments shown and described in detail, it is not intended to be limited to the details shown since various modifications and structural changes may be made without departing in any way from the spirit and scope of the present invention. The embodiments were chosen and described in order to explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein:

1. A method for determining a delay time of a pre-catalytic converter lambda probe during operation of an arrangement with an internal combustion engine, the method comprising the steps of:

supplying a difference between an output signal of the pre-catalytic converter lambda probe and a desired signal to a controller as an input signal;

measuring an output signal of the controller, said output signal determining an air-fuel ratio of the exhaust gas to which the pre-catalytic converter lambda probe is exposed during the operation;

determining a first time when a first output signal of the controller satisfies a first predetermined criterion;

determining a second time following the first time when a second output signal of the pre-catalytic converter lambda probe satisfies a second predetermined criterion;

determining a time difference between the second time and the first time, said time difference defining the delay time; and determining an actual air-fuel ratio of the exhaust gas to which the pre-catalytic converter lambda probe is exposed by determining the output signal of the controller at a time computed by adding the delay time to the second time.

2. The method of claim 1, wherein the first predetermined criterion and the second predetermined criterion are identical.

3. The method of claim 1, wherein the first predetermined criterion is satisfied when the first output signal reaches a maximum at the first time.

4. The method of claim 1, wherein the second predetermined criterion is satisfied when the second output signal reaches a maximum at the second time.

* * * * *